(12) United States Patent
Malkas et al.

(10) Patent No.: US 7,294,471 B2
(45) Date of Patent: Nov. 13, 2007

(54) METHOD FOR PURIFYING CANCER-SPECIFIC PROLIFERATING CELL NUCLEAR ANTIGEN

(75) Inventors: Linda H. Malkas, Indianapolis, IN (US); Robert J. Hickey, Indianapolis, IN (US); Pamela E. Bechtel, Tempe, AZ (US); Min Park, Los Alamos, NM (US); Derek J. Hoelz, Indianapolis, IN (US); Dragana Tomic, Baltimore, MD (US); Lauren Schnaper, Lutherville, MD (US)

(73) Assignee: csKeys, LLC, Indianapolis, IN (US)

( * ) Notice: Subject to any disclaimer, the term of this patent is extended or adjusted under 35 U.S.C. 154(b) by 130 days.

(21) Appl. No.: 10/083,576

(22) Filed: Feb. 27, 2002
(Under 37 CFR 1.47)

(65) Prior Publication Data

US 2003/0162233 A1  Aug. 28, 2003

(51) Int. Cl.
*G01N 33/53* (2006.01)

(52) U.S. Cl. .................. 435/7.1; 435/7.2; 435/7.21; 435/7.23; 435/7.5; 435/7.7; 435/7.9; 435/7.91; 436/518

(58) Field of Classification Search .............. 435/7.1, 435/7.2, 7.21, 7.23, 7.5, 7.7, 7.72, 7.9, 7.91–7.95; 436/518, 523–32
See application file for complete search history.

(56) References Cited

U.S. PATENT DOCUMENTS

| | | | |
|---|---|---|---|
| 4,376,110 A | 3/1983 | David et al. | |
| 4,486,530 A | 12/1984 | David et al. | |
| 4,632,901 A | 12/1986 | Valkirs et al. | |
| 4,727,019 A | 2/1988 | Valkirs et al. | |
| 5,356,817 A | 10/1994 | Cole | |
| 5,395,754 A | 3/1995 | Lambotte et al. | |
| 5,574,047 A | 11/1996 | Bumol et al. | |
| 5,580,903 A | 12/1996 | Mawatari et al. | |
| 5,616,461 A | 4/1997 | Schaffer et al. | |
| 5,756,476 A | 5/1998 | Epstein et al. | |
| 5,889,169 A | 3/1999 | Beach et al. | |
| 6,063,575 A | 5/2000 | Sekowski et al. | |
| 6,093,543 A | 7/2000 | Coll et al. | |
| 6,514,713 B1 * | 2/2003 | Knott et al. | ............... 435/7.23 |
| 2006/0073477 A1 | 4/2006 | Malkas | |

FOREIGN PATENT DOCUMENTS

| | | |
|---|---|---|
| JP | 04012273 | 1/1992 |
| JP | 07191037 | 7/1995 |
| WO | 96/35715 | 11/1996 |

OTHER PUBLICATIONS

Gary et al JBC vol. 272 p. 24522 (1997).—24529.*
Ogata et al, *J. of Immunol.*, 135(4):2623-2627 (1985).

Malkas, "A Cancer Specific Form of Proliferating Cell Nuclear Antigen (csPCNA) Is Present in Malignant Human Cells and Tissues", Abstract, Presented at the MD Anderson Tumor Marker Meeting. Houston, Texas (Mar. 2001).

Macedo et al, "Investigations on the Mechanism of Action of Novel Acylhydrazones and Sulfonylhydrazones Derivatives", *Proceedings of the American Association for Cancer Research*, Abstract No. 431, vol. 42, p. 80 (Mar. 2001).

Abdel-Aziz et al, "Effects of Cytosine Arabinoside, Camptotheein, and Etoposide on In Vitro DNA Replication Mediated by the Human Cancer Cell DNA Synthesome", *Proceedings of the American Association for Cancer Research*, Abstract No. 541, vol. 42, p. 100 (Mar. 2001).

Tomie et al, "Detection of the Cancer Specific Form of PCNA by Elisa Assay", *Proceedings of the American Association for Cancer Research*, Abstract No. 2507, vol. 42, p. 466 (Mar. 2001).

Smith et al, "Visualization of Cervical and Breast Cancer-Derived DNA Replication Complexes by Transmission Electron Microscopy", *Proceedings of the American Association for Cancer Research*, Abstract No. 2795, vol. 42, p. 519 (Mar. 2001).

Lankford et al, "Proteomic Analysis of the Human Breast and Ovarian DNA Synthesome Associated Mismatch Repair Proteins", *Proceedings of the American Association for Cancer Research*, Abstract No. 4797, vol. 42, p. 894 (Mar. 2001).

Hoelz et al, "Isolation and Characterization of the Non-Malignant Form of PCNA from MCF7 Breast Cancer Cells", *Proceedings of the American Association for Cancer Research*, Abstract No. 4798, vol. 42, p. 894 (Mar. 2001).

Hicke et al, "The Human Cell DNA Synthesome: A Novel In Vitro Model System for Evaluating Anticancer Drug Action", Abstract No. 137, *Anticancer Research*, 21:1577-1622 (2001).

Malkas et al, "Specific Functional and Structural Alteration of the Cancer Cells' DNA Replication Apparatus: Potential New Targets for Drug Development", Abstract No. 152, *Anticancer Research*, 21:1577-1622 (2001).

Hoelz et al, "Differential Binding of p21$^{WAF1}$ by an Altered Form of PCNA Present in Breast Cancer Cells", Abstract, San Antonio Breast Cancer Symposium (Dec. 2001).

Bechtel et al, *Advances in Brief, Cancer Research*, 58:3264-3269 (1998).

Beyne-Rauzy et al., "Anti-PCNA Antibodies: Prevalence and Predictive Value," Joint Bone Spine 72:430-36 (2005).

Brand et al., "Autoreactive Epitope Profiles of the Proliferating Cell Nuclear Antigen Define Two Classes of Autoantibodies," J. Immunol. 152:4120-28 (1994).

Dobrolecki et al., Abstract No. 3546 AACR (2004).

Fukuda et al., "Structure-Function Relationship of the Eukaryotic DNA Replication Factor, Proliferating Cell Nuclear Antigen" J. Biol. Chem. 270:22527-34 (1995).

Hoelz et al., "Cancer Specific Proliferating Cell Nuclear Antigen as a Novel Diagnostic Marker for the Detection of Breast Cancer" Abstract http://cdmrp.army.mil/bcrp/era/abstracts2005/0210467_abs.pdf (2005).

(Continued)

*Primary Examiner*—Sheela J. Huff
(74) *Attorney, Agent, or Firm*—Whiteford, Taylor & Preston, LLC; R. Christopher Rueppell

(57) ABSTRACT

A method for purifying cancer-specific Proliferating Cell Nuclear Antigen (csPCNA) is described, as well as an immunoassay based thereon.

15 Claims, 11 Drawing Sheets

OTHER PUBLICATIONS

Hoelz, "Cancer Specific Proliferating Cell Nuclear Antigen as a Novel Diagnostic Marker for the Detection of Breast Cancer—Annual Summary Rept. Oct. 1 2002-Sep. 30, 2003" Abstract http://www.ntis.gov/search/product.asp?ABBR=ADA422005&starDB=GRAHIST.

Kelman, "PCNA: Structure, Functions and Interactions" Oncogene 14:629-40 (1997).

Ino et al., "Expression of Proliferating Cell Nuclear Antigen (PCNA) in the Adult and Developing Mouse Nervous System" Mol. Brain Res. 78:163-74 (2000).

Roos et al., "Determination of the Epitope of an Inhibitory Antibody to Proliferating Cell Nuclear Antigen" Experimental Cell Res. 226:208-13 (1996).

Tzang et al., "Presentation of Autoantibody to Proliferating Cell Nuclear Antigen in Patients with Chronic Hepatitis B and C Virus Infection" Ann. Rheum Dis. 58:630-34 (1999).

Warbrick, "The Puzzle of PCNA's Many Partners" BioEssays 22:997-1006 (2000).

Zhang et al., "The Interdomain Connector Loop of Human PCNA Is Involved in a Direct Interaction with Human Polymerase σ" J. Biol. Chem. 273:713-19 (1998).

Malkas et al., "A Cancer-Specific Form of Proliferating Cell Nuclear Antigen (csPCNA) Is Present in Malignant Human Breast Cells and Tissues" J. Clin. Ligang Assay 25:20-32 (2002).

Hoelz et al., "The Discovery of Labile Methyl Esters on Proliferating Cell Nuclear Antigen by MS/MS" Proteomics 6:4808-16 (2006).

Naryzhny et al., "Observation of Multiple Isoforms and Specific Proteolysis Patterns of Proliferating Cell Nuclear Antigen in the Context of Cell Cycle Compartments and Sample Preparations" Proteomics 3:930-36 (2003).

Almendral et al, Proc. Natl. Acad. Sci., USA, 84:1575-1579(1987).
Applegreen et al, J. of Cell Biochem, 59:91-107 (1995).
Bechtel et al, Proc. of the American Association for Cancer Research, 37:494 (1996).
Brown, Breast Cancer, Hematology/Oncology Clinics of North America, 8(1):101-112 (1994).
Coll et al, Oncology Research, 8(10-11):435-447 (1996).
Coll et al, Oncology Research, 9:629-639 (1997).
Gabizon et al, Cancer Research, 52:891-896 (1992).
Genesis Group Associates, Inc., New tests improve breast cancer prognosis, Genesis Report-Dx, vol. 6, No. 3, NLDB Accession No. 97-320100 (1997).
Hickey et al, "DNA Replication and Mutagenesis", American Soc. for Microbiology, Washington, D.C., pp. 41-54 (1998).
Hickey et al, Critical Reviews in Eukaryotic Gene Expression, 7(1&2):125-157 (1997).
Kang et al, Carcinogenesis, 18(2):251-257 (1997).
Kirpotin et al, Biochemistry, 36:66-75 (1997).
Lasic et al, Science, 267:1275-1276 (1995).
Levenson et al, Cancer Research, 57:3071-3078 (1997).
Lin et al, Cell Growth & Differentiation, 8:1359-1369 (1997).
Lin et al, Leukemia Research, 21(6):501-512 (1997).
Malkas et al, Biochemistry, 29(27):6362-6374 (1990).
Ogata et al, The J. of Immunol., 135(4):2623-2627 (1985).
Papahadjopoulus et al, Proc. Natl. Acad. Sci., USA, 88:11460-11464 (1991).
Park et al, Proc. Natl. Acad. Sci., USA, 92:1327-1331 (1995).
Pohl et al., Neural network evaluation of multiple tumor markers for diagnosis of ovarian cancer (Meeting Abstract), Non-serial, 3rd International Conference of the Mediterranean Society of Tumor Marker Oncology, CANCERLIT Accession No. 95614997 (1994).
Sekowski et al, Toxicology and Applied Pharmacology, 145:268-276 (1997).
Simbulan-Rosenthal et al, Biochem, 35(36):11622-11633 (1996).
Soule et al, Cancer Research, 50:6075-6086 (1990).
Soule et al, J. of the Natl. Cancer Inst., 51(5):1409-1413 (1973).
Stampfer, J. of Tissue Culture Methods, 9(2):107-115 (1985).
Tait et al, Cancer Research, 50:6087-6094 (1990).
Tockman et al, Cancer Research, 52 (Suppl.):2711s-2718s (1992).
Tom et al, J. of Cell. Biochem., 63:259-267 (1996).
Ward, Developmental Oncology, 21:90-106 (1985).
Waseem et al, J. of Cell Science, 96(1):121-129 (1990).
Winter et al, Ann. Rev. Immunol., 12:433-455 (1994).
Sekowski et al, Cancer Res., 58:3259-3263 (1998).
Yagura et al, Biochemistry, American Chemical Society, 26:7749-7754(1987).
Zhigang et al, J. Biological Chemistry, 271(45):28243-28249 (1996).
Ariza et al. Env. & Mol. Mutagenesis, 27:30-33 (1996).
Coll et al, Proc. Natl. Meet. Am. Assoc. Cancer Res. 37:A3409 (1996).
Lin et al, Proc. Natl. Meet. Am. Assoc. Cancer Res., 37:A3413 (1996).
Malkas et al, Proc. Natl. Acad. Sci., USA, 86:70-74 (1989).
Mikita et al, Biochemistry, 27:4698-4705 (1988).
Murakami et al, Proc. Natl. Acad. Sci., USA, 83:6347-6351 (1986).
Roberts et al, Proc. Natl. Acad. Sci., USA, 85:7064-7068 (1988).
Sekowski et al, Proc. Natl. Meet. Am. Assoc. Cancer Res., 38:A270 (1997).
Wu, et al, J. Cell. Biochem. 54: 32-46 (1994).
Lasic and Martin, Stealth Liposomes, (1995) p. 1-3.
Hayes, Recent Results Cancer Res., 140: 101-113 (1996).
Schwartz, et al., Clin. Chem., 39(11B): 2409-2412 (1993).
Haerslev, et al., Breast Cancer Res. Treat., 37: 101-113 (1996).
Schmitt, et al., Path. Res. Pract., 190: 786-791 (1994).
Zaccaria, et al., Leukemia and Lymphoma 16: 231-236 (1995).
Takasaki, et al., J. Natl. Cancer Inst. 73(3): 655-661 (1984).
Thiele, et al., Hematologic Path. 7(4): 239-249 (1993).
Bechtel, Pamela E. Bechtel, *Proliferating Cell Nuclear Antigen in Malignancy*, (May 8, 1998) (Ph.D. Dissertation, University of Maryland) (on file with University of Maryland Health Sciences and Human Services Library).

\* cited by examiner

Analysis of csPCNA Isolation Fractions

Validation of the viability of the streptavidin surface of the streptavidin-coated plate 0) blank
1) 1:1000 000 dilution
2) 1:800 000 dilution
3) 1: 600 000 dilution
4) 1:400 000 dilution
5) 1:200 000 dilution (2 exsp)
6) 1:150 000 dilution
7) 1:100 000 dilution (2 exsp)
8) 1:75000 dilution
9) 1:50 000 dilution (2 exsp)
10) 1:25 000 dilution (2 exsp)
11) 1:10 000 dilution (2 exsp)
12) 1:5000 dilution
13) 1:1500 dilution
14) 1:1000 dilution
15) 1:100 dilution
16) 1:50 dilution ELISA ASSAY with MCF7 P4 and MCF10 P4 proteins ELISA Assay for detection of Cancer Specific Form of PCNA present in MCF7 breast cancer cell lines

US 7,294,471 B2

METHOD FOR PURIFYING CANCER-SPECIFIC PROLIFERATING CELL NUCLEAR ANTIGEN

GOVERNMENT LICENSE RIGHTS

This invention was made with government support under Grant Nos. CA-83199, CA-57350-04, and CA-74904 awarded by NIH and Grant No. DAMD-17-97-1-7037 awarded by Department of Defense. The government has certain rights in the invention.

FIELD OF THE INVENTION

The present invention is directed to a method for purifying cancer-specific Proliferating Cell Nuclear Antigen (csPCNA), as well as to an ELISA for distinguishing csPCNA from native-proliferating cell nuclear antigen (nPCNA) and diagnosing cancer.

BACKGROUND OF THE INVENTION

A. Cancer

One of the least understood and most complex disease processes is the transformation that occurs as a cell becomes malignant. This process involves both genetic mutations and proteomic transformations, the result of which allows the cell to escape normal controls preventing inappropriate cell division. All cancers are unique and distinct from other cells, as well as other cancers. Despite this uniqueness, cancer cells share some common attributes. Most cancer cells proliferate outside of the normal cell cycle controls, exhibit morphological changes and exhibit various biochemical disruptions to cellular processes.

Cancer is usually diagnosed when a tumor becomes visible well after the first on-set of cellular changes. Many cancers are diagnosed after a biopsy sample is examined by histology for morphologic abnormalities, evidence of cell proliferation and genetic irregularities. There is a clear need to identify and characterize new markers for malignancy. Recently there has been an effort to define markers for the diagnosis and prognosis of malignancies. Many of the genetic and biochemical changes occur during the early development of a tumor and these changes should be exploited for the early diagnosis of cancer.

Breast cancer is the leading cause of death among women in the Western world. Recent data suggests that there is a strong correlation between late detection and poor prognosis of this disease. Analysis of a thousand clinical cases indicates that there is extensive genetic damage and a high rate of DNA synthesis in breast tumors in comparison with normal breast tissue. These data suggest that an alteration in the DNA replication machinery of breast cancer cells may contribute to uncontrolled and error-prone DNA synthesis.

Human breast cells mediate DNA synthesis using the multiprotein replication complex termed the DNA synthesome (Coll et al, *Oncology Research*, 8:435-447 (1996)). The DNA synthesome is fully competent to support in vitro DNA replication. The transformation of non-malignant human breast cells to a malignant state is accompanied by an alteration to a specific component of DNA synthesome, Proliferating Cell Nuclear Antigen (PCNA). PCNA is a well-known cell-cycle marker protein, originally identified as an antigen for autoimmune disease (Bechtel et al, *Cancer Research*, 58:3264-3269 (1998)).

B. PCNA in Cancer/other Cell Processes

PCNA is currently used in the diagnosis of malignancy, as well as in evaluating the prognosis of the patient (Schonborn et al, *J. Cancer Res. Clinical Oncology*, 121:122 (1995)). PCNA is a small (36 kD) nuclear protein involved in many cellular processes. PCNA plays crucial roles in both DNA replication and DNA repair mechanisms. PCNA has also been associated with transcription events. PCNA forms a trimer in the nucleus and acts as an accessory protein to polymerase δ, and also interacts with a variety of other proteins (Downey et al, *Cancer Cells*, 6:1211-1218 (1988)). In the evaluation of malignancy, PCNA is often used as a marker for cell proliferation. However, PCNA alone does not correlate with the stage of malignancy or the patient outcome.

A novel PCNA from breast cancer cells has been identified. The malignant breast cancer cells express a unique, acidic form of PCNA protein, i.e., csPCNA, which can clearly be distinguished from the basic form of this protein found in non-malignant cells, i.e., nPCNA. This alteration is most likely the result of a post-translational modification (Bechtel et al, *Cancer Res.*, 58:3264-3269 (1998)). However, prior to the present invention an effective method to purify csPCNA has not been described.

Recent advances in biochemical and genetic studies strongly indicate that PCNA may interact with different proteins involved in DNA mismatch repair, Okazaki fragments ligation, DNA methylation and chromatin assembly (Balajee et al, *Mutat. Res.*, 404:3-11 (1998); Ceccotti et al, *Curr Biol:* 6:1528-1531 (1996); Chen et al, *Proc. Natl. Acad. Sci., USA*, 93:11597-11602 (1996); Chuang et al, *Science*, 277:1996-2000 (1997); Dimitrova et al, *J. Cell. Biol.*, 146:709-722 (1999); Eki et al, *J. Biol. Chem.*, 266:3087-3100 (1991); Eki et al, *J. Biol. Chem.*, 267:7284-7294 (1992); Greene et al, *Hum Mol Genet:* 8, 2263-2273 (1999); Gu et al, *Nucleic Acids Res.*, 26:1173-1178 (1998); Henderson et al, *Embo J.*, 13:1450-1459 (1994); Johnson et al, *J. Biol. Chem.*, 271:27987-27990 (1996); Kelman, *Oncogene*, 14:629-640 (1997); Kolodner et al, *Curr. Opin. Genet. Dev.*, 9:89-96 (1999); Krude, *Curr. Biol.*, 9:R394-R396 (1999); Lee et al, *J. Biol. Chem.*, 266:22707-22717 (1991); Levin et al, *Proc. Natl. Acad. Sci., USA*, 94:12863-12868 (1997); Levin et al, *Curr. Biol.*, 10:919-922 (2000); Martini et al, *J. Cell. Biol.*, 143:563-575 (1998); Merrill et al, *Genetics*, 148:611-624 (1998); Mimura et al, *Genes Cells*, 5:439-452 (2000); Miura, *J. Radiat. Res. (Tokyo)*, 40:1-12 (1999); Moggs et al, *Mol. Cell. Biol.*, 20:1206-1218 (2000); Nishikawa et al, *Jpn. J. Cancer. Res.*, 88:1137-1142 (1997); Otterlei et al, *Embo J.*, 18:3834-3844 (1999); Pan et al, *Proc. Natl. Acad. Sci., USA*, 90:6-10 (1993); Schweitzer et al, *Genetics*, 152:953-963 (1999); Shibahara et al, *Cell*, 96:575-85 (1999); Sinicrope et al, *Clin. Cancer. Res.*, 4:1251-1261 (1998); Tom et al, *J. Biol. Chem.*, 276:24817-24825 (2001); Tomkinson et al, *Mutat. Res.*, 407:1-9 (1998); Tsurimoto, *Front. Biosci.*, 4:D849-D858 (1999); Umar et al, *Cell*, 87:65-73 (1996); and Wu et al, *Nucleic Acids Res.*, 24:2036-2043 (1996)).

Xeroderma Pigmentosum (XP)G protein is reported to interact with PCNA (Gary et al, *J. Biol. Chem.*, 272(39): 24522-24529 (1997)). The DNA repair endonuclease XPG binds to proliferating cell nuclear antigen (PCNA) and shares sequence elements with the PCNA-binding regions of FEN-1 and cyclin-dependent kinase inhibitor p21. XPG is a repair endonuclease similar to FEN-1 and required for nucleotide excision repair. The human XPG endonuclease cuts on the 3' since of a DNA lesion, during nucleotide excision repair.

In the present invention, XPG protein was unexpectedly found to be useful in selectively purifying csPCNA, and as a part of an ELISA system which can distinguish the csPCNA from the nPCNA. The detection of csPCNA in the ELISA serves as a powerful marker for early detection of malignancy.

SUMMARY OF THE INVENTION

An object of the present invention is to provide a method for selectively purifying csPCNA.

Another object of the present invention is to provide an ELISA for detection of csPCNA and early detection of malignancy.

The above-described objects, as well as others, which will be apparent from the detailed description of the invention provided hereinafter, have been met in one embodiment by a method for purifying csPCNA comprising the steps of:
  (A) obtaining a tissue or body fluid sample comprising csPCNA;
  (B) contacting said sample with a peptide comprising the amino acid sequence LeuLysGlnLeuAspAla-GlnGlnThrGlnLeuArg IleAspSerPhePheArgLeuAla-GlnGlnGluLys GluAspAlaLysArg (SEQ ID NO:1), wherein said peptide is immobilized on a solid support and binds to said csPCNA to form a peptide-csPCNA complex; and
  (C) isolating csPCNA from said peptide-csPCNA complex so as to purify said csCNA.

In another embodiment, the above-identified objects have been met by an immunoassay for detecting csPCNA comprising:
  (1) contacting a test sample with a peptide comprising the amino acid sequence LeuLysGlnLeuAspAla-GlnGlnThrGlnLeuArgIle AspSerPhePheArgLeuAla-GlnGlnGluLysGluAsp AlaLysArg (SEQ ID NO:1), which has been immobilized on a solid support so as to bind csPCNA to said peptide to form a peptide-csPCNA complex; and
  (2) contacting said peptide-csPCNA complex with an anti-PCNA antibody and detecting binding of said antibody to said complex.

DETAILED DESCRIPTION OF THE INVENTION

Figure 1:
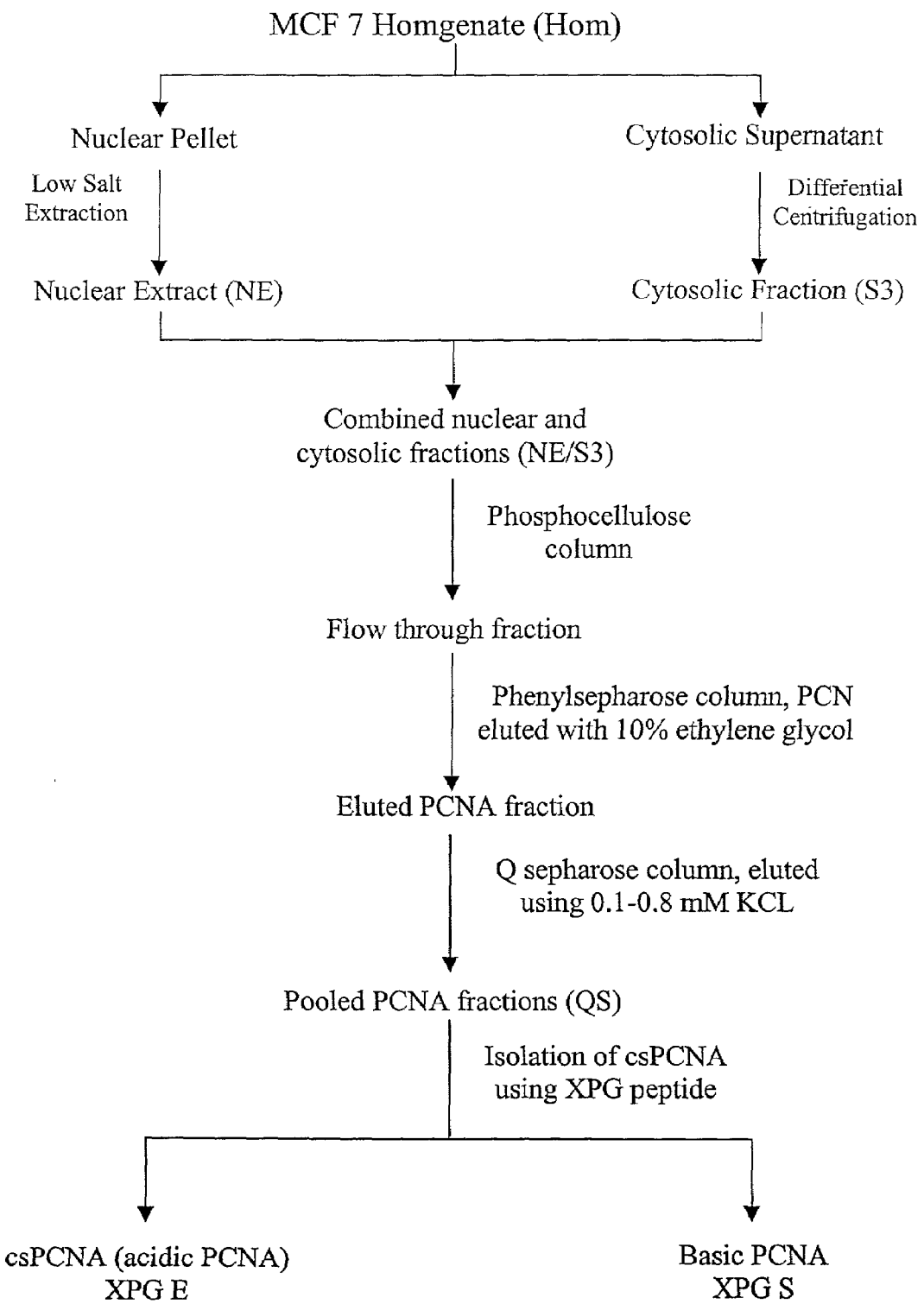
FIG. 1 shows a flow chart depicting steps involved in the isolation of total PCNA and csPCNA.

As discussed above, in one embodiment, the above-described objects of the present invention have been met by a method for purifying csPCNA comprising the steps of:
  (A) obtaining a tissue or body fluid sample comprising csPCNA;
  (B) contacting said sample with a peptide comprising the amino acid sequence LeuLysGlnLeuAspAla-GlnGlnThrGlnLeuArg IleAspSerPhePheArgLeuAla-GlnGlnGluLys GluAspAlaLysArg (SEQ ID NO:1), wherein said peptide is immobilized on a solid support and binds to said csPCNA to form a peptide-csPCNA complex; and
  (C) isolating csPCNA from said peptide-csPCNA complex so as to purify said csCNA.

Preferably, prior to step (B), the thus obtained tissue or body fluid sample of step (A) is subjected to a process comprising the steps of:
  (1) homogenizing cells constituting said tissue or body fluid to obtain a homogenate (H);
  (2) separating said H into a nuclear pellet fraction (NP) and a cytosolic fraction (S1);
  (3) extracting nuclei from said NP to obtain a nuclear extract (NE);
  (4) subjecting said S1 to centrifugation to obtain a post-mitochondrial cytosolic supernatant (S2);
  (5) subjecting said S2 to centrifugation to obtain a post-mitochondrial/post-microsomal cytosolic supernatant (S3);
  (6) combining said NE and said S3 to form an NE/S3 fraction, applying the resulting NE/S3 fraction to a phosphocellulose (a weak anion exchange matrix) column and collecting the flow through (PCFT);
  (7) applying the resulting PCFT to a phenylsepharose (a hydrophobic chromatography matrix) column, eluting the column with buffer comprising ethylene glycol and collecting the eluant (PSE);
  (8) dialyzing out ethylene glycol present in the PSE to obtain a dialyzate; and
  (9) applying the resulting dialyzate to a Q-Sepharose (a strong anion exchange matrix) column, eluting with a dialyzate buffer comprising a salt gradient, and collecting and pooling PCNA-containing fractions to obtain said sample.

More preferably, the tissue or body fluid sample of step (A) further comprises native-PCNA (nPCNA), said nPCNA does not bind to said peptide in step (B) but flows through the column (XPGS), whereas csPCNA binds to said peptide in step (B) to form a peptide-csPCNA complex and in step (C) isolating csPNA is effected using an elution buffer whereby csPCNA is eluted from said csPCNA-complex (XPGE).

The particular tissue or body fluid sample which is employed in the present invention is not critical thereto.

Examples of tissue which can be employed in the present invention include cervical, mammary glands, esophageal, glial cells, lung, stomach, intestine, prostate, and white blood cells. Examples of body fluid which can be employed in the present invention include urine, serum and whole blood.

The source of the tissue or body fluid is from a subject afflicted with a cancer. The particular cancer is not critical to the present invention. The cancers can be carcinomas, sarcomas, lymphomas, or leukemias. Examples of such cancers include cervical carcinoma, mammary gland carcinoma of ductal or lobular origin, gliomas, prostate, lung, esophageal, stomach, and ovarian cancer.

In step (B) the solid support employed is critical to the present invention, because the XPG peptide of SEQ ID NO:1 can be expressed as a fusion protein, e.g., a GST fusion (GST=glutathione-S-transferase), and the support will depend on the fusion partner. An example of the solid support which can be employed in this case include Glutathione Sepharose (Pharmacia). However, expression of the XPG-fusion protein in a Calmodulin or 6× His (oligo (6×) histidine) format can also be used in the present invention.

In step (C), csPCNA is isolated from the complex by, for example, elution with buffer comprising 50 mM Tris-HCl (pH 8.0). Again, nPCNA does not bind to the column matrix, but flows through the column and appears in the flow-through liquid exiting the column while the complex and contaminating proteins are being loaded onto the column.

The peptide represented by SEQ ID NO:1 may be synthesized chemically or by recombinant DNA techniques, as described by Gary et al, *J. Biol. Chem.*, 232:24522-24529 (1997). Further, as noted above, the peptide may be in the form of a fusion protein. The partner of the fusion protein is not critical to the present invention. Examples of such partners include Glutathione-S-Transferase (GST), Calmodulin Binding protein, and oligo(6×) histidine.

The resulting preferred csPCNA can be used to produce antibodies (monoclonal or polyclonal) specific for csPCNA by conventional techniques. The resulting purified csPCNA can also be used as standards for diagnostic kits, as well as enabling development of specific inhibitors for csPCNA (not nPCNA), the identification of the site(s) on the PCNA polypeptide that is (are) modified in nPCNA, provide the baseline for comparison to identify the type of modification sustained by nPCNA and lacking from csPCNA, the identification of specific metabolic pathways that mediate the addition or removal of this (these) post-translational modifications.

Products of antibodies specific for csPCNA can be produced by challenging mammals (e.g., rabbits, goats, horses, etc) with the peptide sequence which is post-translationally modified in nPCNA, but not in csPCNA. All commercially available antibodies to PCNA that exist to date (~10) recognize the interdomain connector loop. They cannot distinguish csPCNA from nPCNA. Identification of the amino acid sequence of PCNA that is bound by the XPG peptide only in the csPCNA form of PCNA provides the target for preparing selective antibodies recognizing only csPCNA.

Specific inhibitors of csPCNA's interaction with their target proteins can be produced by construction or expression of peptides identical to the interacting domains of csPCNA and by computational chemistry methods. Through computational chemistry, the sites of interactions can be modeled and searches of existing 3-D chemical library structures or the design of new compounds can be made to disrupt and/or promote interaction between csPCNA and the proteins.

Using mass spectrometry peptide analysis of tryptic fragments of csPCNA and nPCNA will identify the fragments (peptides) that are unique to csPCNA. Sequence identification of these peptides using LC/MS-TDF mass spectrometry will identify the sequence, and thus the position of the modified peptides or amino acids within nPCNA that are modified in csPCNA (or that are modified in csPCNA and are not modified in nPCNA).

Figure 8:
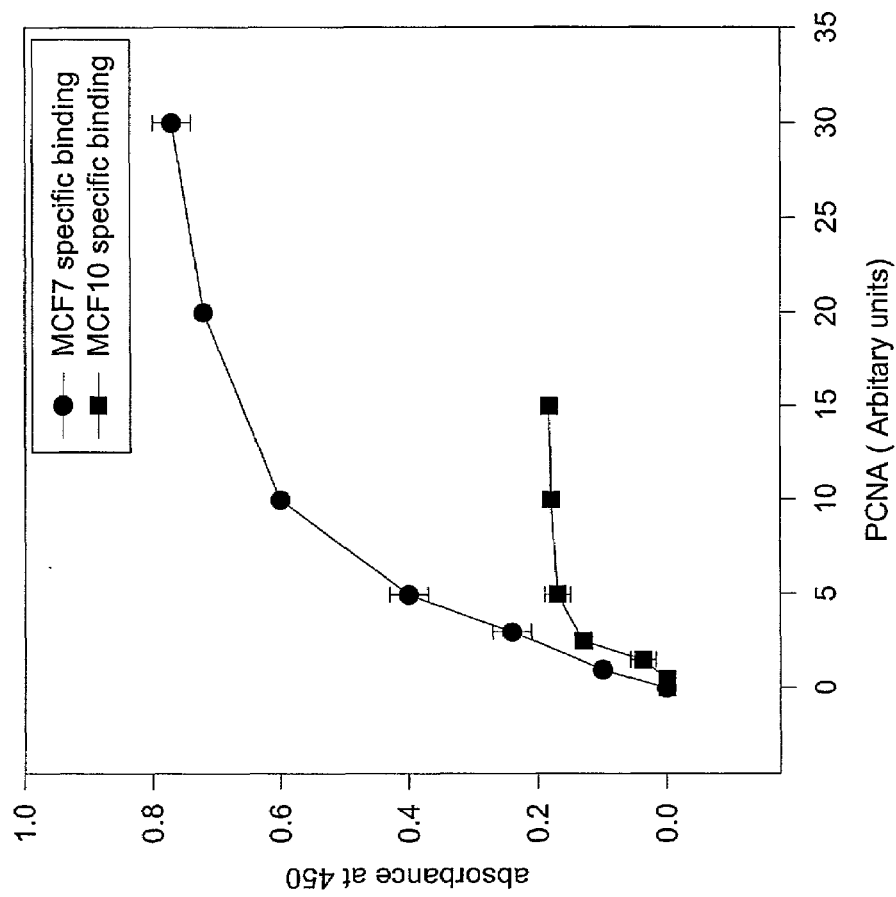
FIG. 8 shows the results of an ELISA assay comparing the abundance of csPCNA in extracts of MCF7 (malignant) cells and MCF 10A (normal) cells.

Furthermore, molecular weight and sequence analysis of these peptides by mass spectroscopy will indicate what types of post-translational modifications have been sustained by csPCNA and/or nPCNA. The identification of these post-translational modifications then leads to the pathways and/or enzymes and/or other molecules responsible for either the addition of the modification or the loss of the modification from the csPCNA. In addition, computer analysis of the amino acid domains of the csPCNA that interact with the XPG peptide can reveal the presence of specific consensus sequences for a particular type of post-translational modification.

csPCNA is believed to be a better diagnostic/prognostic indicator for cancer than current methodologies which measure total PCNA. This is because total PCNA of malignant tissue/cells takes into account nPCNA and csPCNA, while this method of diagnostic/prognostic indication detects a form of PCNA only found in malignant cells/tissue. Based upon the abundance of the cancer specific form of csPCNA relative to the abundance of nPCNA the degree or extent of malignancy can be estimated. Using an ELISA assay, e.g., one whose results are shown in FIG. 8, the abundance of PCNA can be measured relative to a set of standards of csPCNA of varying abundance. Comparison of the experimentally determined absorbance (using the ELISA) for the sample to the absorbance of the standards can be used to indicate the abundance of the csPCNA in the sample.

Accordingly, in another embodiment, the above-described objects of the present invention have been met by an immunoassay for detecting csPCNA comprising:

(1) contacting a test sample with a peptide comprising the amino acid sequence LeuLysGlnLeuAspAla-GlnGlnThrGlnLeuArgIle AspSerPhePheArgLeuAla-GlnGlnGluLysGluAsp AlaLysArg (SEQ ID NO:1), which has been immobilized on a solid support so as to bind csPCNA to said peptide to form a peptide-csPCNA complex; and (2) contacting said peptide-csPCNA complex with an anti-PCNA antibody and detecting binding of said antibody to said complex.

The particular test sample employed is not critical to the present invention and may include any of the tissue or body fluid samples discussed above.

The particular format of the immunoassay of the present invention is not critical to the present invention. Examples of such formats include an ELISA, radio-immuno assay, dot blot assay, slot blot assay, immunoprecipitation and protein quantification, immuno-PCR, and Western blot.

Antibodies to PCNA can be prepared by challenging mammals (e.g., rabbits, goats, horses, etc) with the peptide sequence which is post-translationally modified in nPCNA, but not in csPCNA. All commercially available antibodies to PCNA that exist to date (~10) recognize the interdomain connector loop. They cannot distinguish csPCNA from nPCNA. Identification of the amino acid sequence of PCNA that is bound by the XPG peptide only in the csPCNA form of PCNA provides the target for preparing selective antibodies recognizing only csPCNA.

The detectable enzyme employed in the ELISA is not critical to the present invention. Examples of such detection enzymes include horse radish peroxidase and alkaline phosphatase.

As discussed above, the partner of the fusion protein is not critical to the present invention and examples of such partners include GST, Calmodulin Binding Protein and oligo(6x)histadine.

The particular mode of immobilization of the fusion protein on the solid support is not critical to the present invention.

It is preferable that the fusion protein is immobilized on the solid support via biotin-streptavidin conjugation.

The following examples are provided for illustrative purposes only, and are in no way intended to limit the scope of the present invention.

EXAMPLE 1

Isolation of Total PCNA

Total PCNA was isolated using a series of centrifugation and chromatographic steps as shown in FIG. 1, and discussed in detail below.

A. Nuclear Extract (NE)

Human breast cancer cells, MCF7 cells (ATCC No. HTB-22), were grown in DMEM which was supplemented with 10% (v/v) fetal bovine serum, 1.0% (w/w) penicillin/streptomycin, and non-essential amino acids, and then frozen until use.

13.9 g of MCF7 cells were resuspended in 1 volume of homogenization buffer comprising 200 mM sucrose, 50 mM HEPES (pH 7.5), 5.0 mM KCl, 2.0 mM DTT and 0.1 mM PMSF, and dounce homogenized for 30 strokes. The homogenate (H) was then centrifuged at 3000 rpm for 10 min, the cytosolic supernatant removed (S1) and 10 ml of nuclear extraction buffer comprising 50 mM KCl, 50 mM HEPES (pH 7.5), 5.0 mM $MgCl_2$, 5.0 mM EDTA, 5.0 mM EGTA, 1.0 mM DTT and 0.1 mM PMSF, was added to the nuclear pellet.

The resulting nuclear pellet was rocked at 4° C. for 2 hour. The nuclear pellet was centrifuged at 2,500 rpm for 10 min. The resulting supernatant was removed and centrifuged at 100,000×g in a Ti50.2 rotor for 1 hr. The resulting supernatant, i.e., nuclear extract (NE), was collected.

EDTA and EGTA were added to S1 to 5.0 mM, and the resulting fraction was centrifuged in an SS34 rotor at 17,000×g for 15 min. The resulting post-mitochondrial supernatant (S2) was collected, and centrifuged at 100,000×g for 1 hr in a Ti50.2 rotor. The resulting post-mitochondrial and post-microsomal cytosolic supernatant (S3), was collected.

The NE was then combined with the S3 to obtain an NE/S3 fraction.

B. Phosphocellulose Column

Phosphocellulose (PC) was resuspended in a low salt buffer (LS) comprising 200 mM KCl, 50 mM HEPES (pH 7.5), 5.0 mM $MgCl_2$, 1.0 mM DTT and 0.1 mM PMSF. A 20 ml column was poured and attached to a BioRad Biologic system. 25 ml of the NE/S3 fraction was loaded onto the column, and the flow through (PCFT) collected. A low salt fraction (PCLS) was then collected by washing the column with 150 ml of LS buffer. A high salt fraction (PCHS) was then by washing the column collected with 150 ml of high salt buffer (HS) comprising 1.0 M KCl, 50 mM HEPES (pH 7.5), 5.0 mM $MgCl_2$, 1.0 mM DTT and 0.1 mM PMSF. The fractions were analyzed by Western blot analysis as described below, to determine which fractions contained PCNA.

C. Phenylsepharose Column

A phenylsepharose column (PS) was prepared as directed by the manufacturer (Sigma Chemical Co.) and a 6.0 ml column was poured. The column was incubated with 40 ml pre-equilibration buffer comprising 20 mM potassium phosphate (pH 7.0), 0.5 mM EDTA, 0.1 mM EGTA, 10% (v/v) glycerol, 1.0 M ammonium sulfate and 1.0 mM DTT, then the identified PCNA-containing fraction from the PC column was adjusted to 1.0 M ammonium sulfate and applied to the PS column. The PS column was washed with 40 ml of wash buffer comprising 20 mM potassium phosphate, 0.5 mM EDTA, 0.1 mM EGTA, 10% (v/v) glycerol, 0.5 M ammonium sulfate and 1.0 mM DTT (PSW), and the flow through collected (PSFT). Fractions were eluted with 40 ml of elution buffer comprising 20 mM potassium phosphate (pH 7.0), 0.5 mM EDTA, 0.1 mM EGTA, 20% (v/v) glycerol, 10% (v/v) ethylene glycol and 1.0 mM DTT (PSE).

The PSE fractions were dialyzed in a 0.5 M KCl buffer comprising 0.5 M KCl, 50 mM HEPES (pH 7.5), 1.0 mM of protease inhibitor cocktail (Sigma Chemical and/or Behringer-Mannheim and/or Calbio-Chem), 5.0 mM $MgCl_2$ and 1.0 mM DTT; a 0.2 M KCl buffer comprising 0.2M KCl, 50 mM HEPES (pH 7.5), 1.0 mM of a protease inhibitor cocktail (Sigma Chemical and/or Behringer-Mannheim and/or Calbio-Chem), 5.0 mM $MgCl_2$ and 1.0 mM DTT; and TDEG buffer comprising 50 mM Tris (pH 7.5), 1.0 mM DTT, 1.0 mM EDTA, and 10% (v/v) glycerol, and containing 100 mM KCl. The fractions were then analyzed by Western Blot, as described below, to determine which fractions contained PCNA, and the PCNA-containing fractions were combined.

D. Q-Sepharose Column

A 5.0 ml Q-Sepharose column (BioRad) was attached to a BioRad Biologic system. The combined PCNA-containing fractions from the PS column were concentrated to 12.5 ml, and then applied to the column. Fractions (1.0 ml) were eluted using TDEG buffer with a salt gradient of 0.1 M KCl to 0.6 M KCl. The resulting fractions (QS) were analyzed by Western blot, as described below, and the PCNA-containing fractions were combined.

E. Western Blot Analysis

Western blot analysis was performed as described by Bechtel et al, *Cancer Res.,* 58:3264-3269 (1998). Specifically, Western blot analysis was performed using an antibody against PCNA (Amersham) 1:1000, anti-mouse 1:3000 (Amersham) and detection using chemiluminesence (Pharmacia).

Figure 2:
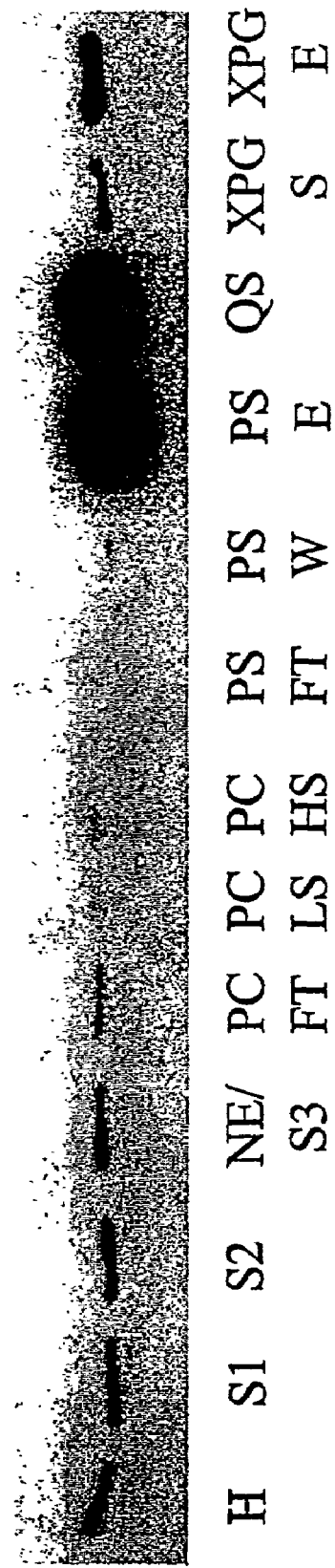
FIG. 2 shows a Western blot of fractions collected during the isolation of PCNA. The fractions were separated on a 10% (w/v) SDS-PAGE gel, transferred to nitrocellose and analyzed using anti-PCNA antibodies. Lane 1: H; Lane 2: S1; Lane 3: S2; Lane 4: NE/S3; Lane 5: PCFT; Lane 6: PCLS; Lane 7: PCHS; Lane 8: PSFT; Lane 9: PSW; Lane 10: PSE; Lane 11: QS; Lane 12: XPGS; Lane 13: XPGE.
Figure 3:
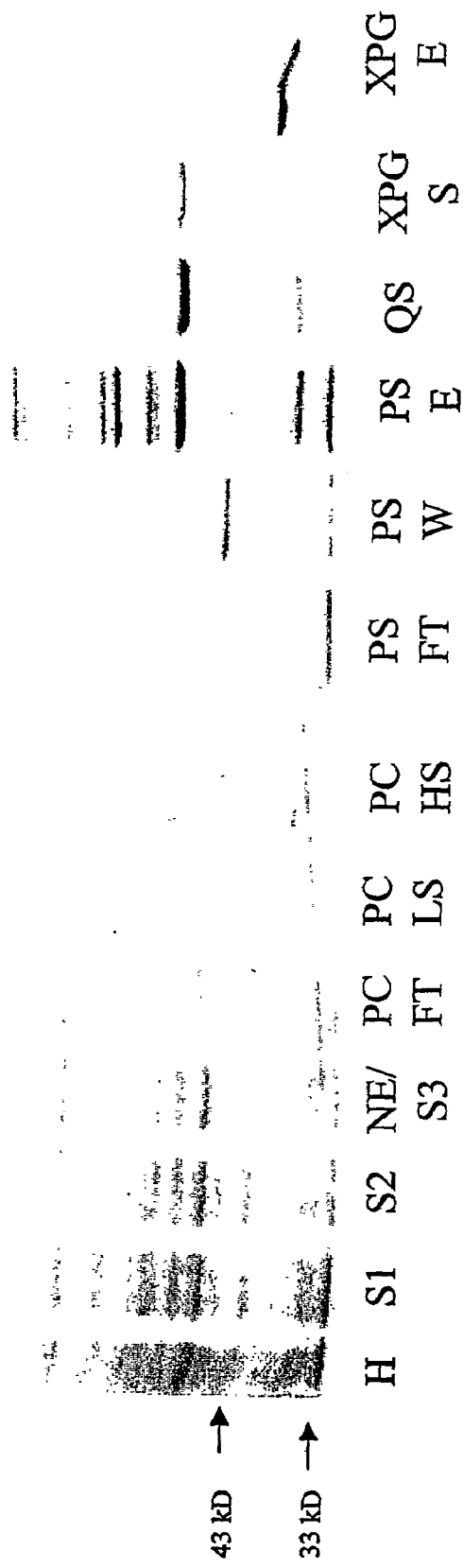
FIG. 3 shows a Coomasie stained gel of fractions collected during the isolation of PCNA. The fractions were separated on a 10% (w/v) SDS-PAGE gel, and then stained with Coomasie blue. Lane 1: H; Lane 2: S1; Lane 3: S2; Lane 4: NE/S3; Lane 5: PCFT; Lane 6: PCLS; Lane 7: PCHS; Lane 8: PSFT; Lane 9: PSW; Lane 10: PSE; Lane 11: QS; Lane 12: XPGS; Lane 13: XPGE.

The fractions collected at all of the steps of the purifications process were run on a 10% (w/v) SDS-PAGE gel, transferred to nitrocellulose and examined by Western blot analysis (FIG. 2) using an antibody against PCNA or stained using Coomasie blue (FIG. 3).

As shown in FIG. 2, PCNA was present in all of the fractions through the phosphocellulose flow through (PCFT). Low levels of PCNA were found in phosphocellulose low salt (PCLS) and high salt (PCHS) fractions, but were undetectable in the 10 µg/ml samples loaded onto the gel. PCNA becomes concentrated in the phenylsepharose eluant (PSE) and Q-sepharose (QS) fractions. The stained gels (FIG. 3) illustrate that at each step, PCNA was further purified through the Q-sepharose column.

EXAMPLE 2

Isolation of csPCNA

The purified total PCNA from the Q-sepharose column was subjected to extraction using a 29 amino acid peptide (SEQ ID NO:1) derived from protein XPG, which had been fused to a GST tag. This portion of the XPG protein, i.e., amino acids 981-1009, has been shown to bind PCNA (Gary et al, supra).

A. Isolation of GST-XPG Fusion Protein

A peptide fragment of the protein XPG was cloned into *E. coli* as a GST fusion protein, as described by Gary et al, supra.

The transformed bacteria were grown overnight in a shaker at 37° C. in 500 ml of Terrific broth comprising 23.5 g Terrific broth powder (Life Technologies Inc., Gaithersburg, Md.), 2.0 ml glycerol and 100 µg/ml Ampicillin. GST expression was induced by adding 0.1 IPTG to the culture and incubating for 4 hrs. The bacteria were collected by centrifugation in a GS lite rotor at 5000 rpm for 10 min. The pellet was resuspended in PBS and centrifuged in a SS34 rotor at 5000 rpm for 10 min. The pellet was resuspended in B-Per (Pierce, Rockford, Ill.), rocked at room temperature for 10 min and centrifuged at 27,000×g for 10 min in a SS34 rotor. The supernatant, i.e., bacterial lysate, was collected.

Glutathione Sepharose 4B matrix beads were resuspended in the storage buffer supplied by the manufacturer, 2.0 ml of the resuspended beads were washed 10 volumes of 4° C. PBS, pelleted, and then the beads were resuspended in 1.0 ml of cold PBS. The resulting GST beads were incubated with the bacterial lysate for 30 min at room temperature and centrifuged in a table top centrifuge at 2500 rpm to obtain GST-XPG-glutathione beads.

B. Purification of PCNA

The resulting GST-XPG-glutathione beads were equilibriated in $T_{50}K_{300}/P_{100}$ buffer comprising 50 mM Tris (pH 7.5), 300 mM KCl and 100 mM potassium phosphate (pH 7.4). The beads were then incubated with the PCNA-containing fractions from the Q-Sepharose column for 30 min at 4° C. and centrifuged at 2500 rpm in a table top centrifuge. The supernatant was decanted and the beads were washed with equilibriation buffer comprising 50 mM Tris (pH 7.5), 300 mM KCl and 100 mM potassium phosphate (pH 7.4) (XPGS). PCNA was eluted by incubating the beads with elution buffer comprising 50 mM Tris (pH 7.5) for 30 min at 4° C., centrifuging in a microfuge and collecting the supernatant (XPGE). The wash (XPGS) and eluant (XPGE) were examined by Western blot, as described above, for the presence of PCNA, and by Coomasie staining. The results are shown in FIGS. 2 and 3.

As shown in FIG. 2, both XPGE and XPGS fractions contained PCNA. Further, as shown in FIG. 3, only a single protein was present in the XPGE fraction and only a few proteins were present in the XPGS fractions.

C. 2D PAGE

The XPGE was further analyzed by 2D PAGE as described below, to determine which form of PCNA was present.

2D PAGE was performed as described by Bechtel et al, supra. Specifically, XPGE (20-40 µg of protein) was loaded onto a first-dimension tube gel comprising 9.2 M urea, 4.0% (w/v) acrylamide, 2.0% (v/v) ampholytes (pH 3-10), and 20% (v/v) Triton X-100. The polypeptides were separated along a pH gradient created using 100 mM NaOH and 10 mM $H_3PO_4$. The tube gels were then placed onto an 8.0% (w/v) acrylamide-SDS gel, and the polypeptides were resolved by molecular weight. The proteins were then examined by Western blot as described above. The results are shown in FIG. 4.

Figure 4:
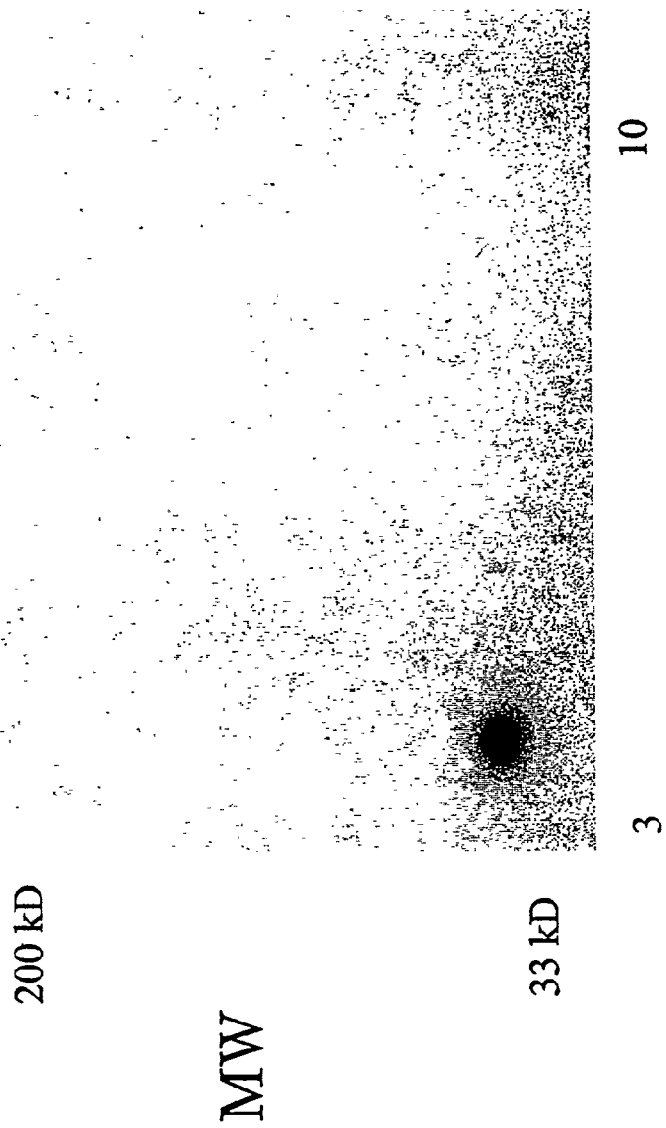
FIG. 4 shows the results of XPGE which was subjected to 2-dimensional SDS-PAGE and Western blot analysis to identify which form of PCNA was present.

As shown in FIG. 4, csPNCA is the only form of PCNA present in the XPGE fraction.

D. Polymerase Assays

DNA polymerase δ activity was measured as described by Han et al, *Biochem. Pharm.*, 60:403-411 (2000). csPCNA has the ability to stimulate the processivity of pol δ, as measured using the assay conditions described by Han et al, supra. More specifically, poly[dG-dC]/[dG-dC] was used as the template, at a concentration of 0.2 $OD_{260}$ units/ml, and the reaction mixture contained 1.0-2.0 µg of purified DNA synthesome protein, 10 mM $MgCl_2$, 10 mM dCTP, 25 mM HEPES (pH 5.9), 200 µg/ml of bovine serum albumin, 100 µCi/ml of [$^{32}$P]dGTP, and 5.0% (v/v) glycerol. The poly [dG-dC]/[dG-dC] template was boiled for 5 minutes and chilled on ice prior to use in the assay. The reaction mixture containing these components was incubated at 37° C. for 15 minutes, and then spotted onto Whatman DE81 filters (Whatman International Ltd, Maidstone, England). The amount of radiolabelled nucleotide bound to the filters was quantified after washing the filters with 10 ml per filter of 0.3 M NaPPi (pH 7.5); followed by washing the filters three times with 10 ml per filter of 0.1 M $NH_4$ formate (pH 7.4). Afterwards, the filters were given a final wash in 95% (v/v) ethanol and then air dried, placed in scintillation vials, covered with 3 ml of scintillation fluid, and placed in a Packard TriCarb 2100TR scintillation counter (Packard Instruments Co., Meriden, Conn.).

The results of this assay demonstrate that addition of PCNA to purified polymerase δ increases the processivity of polymerase δ (See Bravo et al, *Nature*, 326:515-517 (1987); Downey et al, *Cancer Cells*, 6:1211-1218 (1988); and Tan et al, *Proc. Natl. Acad. Sci., USA*, 90:11014 (1986)). The addition of csPCNA to purified polymerase δ was found to increase its processitivity as reported (Tan et al, supra). The addition of csPCNA to the synthesome preparation did little to increase processitivity, presumably because the synthesome contains bound PCNA.

EXAMPLE 3

ELISA Assay

A. Isolation of GST-XPG Fusion Protein

The PCNA binding domain of XPG (SEQ ID NO:1) was ligated into a pGEX-4T-1 expression vector (Amersham Pharmacia Biotech, Inc., Piscataway, N.J.). Recombinant protein was expressed in BL21 (DE3) *Escherichia coli* using 0.8 mM IPTG. Cells were lysed using B-Per reagents (Pierce, Rockford, Ill.); the lysate was incubated with glutathione-agarose beads for 2 hours at 4° C. and subsequently centrifuged for 10 minutes at 3000 rpm. The lysate was washed twice with PBS followed by elution with 10 mM reduced glutathione (Sigma, Co., St. Louis, Mo.) in 50 mM Tris-HCl (pH 7.4).

The resulting purified XPG-GST was biotinylated using a commercial ECL protein biotinylation kit (Amersham Pharmacia Biotech. Inc., Piscataway, N.J.). Briefly, 1.0 mg of protein was diluted in 1.0 ml of biocarbonate buffer (pH 8.6), and incubated for 1 hour at room temperature, in 30 µl of biotinylation reagent per mg of protein. After incubation, the protein sample was applied to a Sephadex G25 column and eluted with 5.0 ml of PBS (pH 7.4). Fractions of biotinylated XPG-GST protein were then collected.

The protein profile of the biotinylated XPG-GST protein was analyzed by 12% (w/v) SDS-PAGE and Silver-Stain procedure (Bio-Rad silver stained plus kit, Bio-Rad, Hercules, Calif.). To determine the presence of XPG-GST protein, an anti-GST antibody (Amersham Pharmacia Biotech, Inc., Piscataway, N.J.) was used at a 1:1000 dilution, followed by HRP-labeled anti-goat IgG (Santa Cruz Biotechnology, Inc., Santa Cruz, Calif.) at a 1:12,000 dilution in 10% (v/v) blocking buffer. The presence of biotinylated fraction of XPG-GST protein was detected using streptavidin-horse radish peroxidase conjugated protein (Amersham Pharmacia Biotech, Inc., Piscataway, N.J.) at dilution of 1:6,000 in PBST. Immunodetection was performed using ECL Western Blotting Detection Kit (Amersham Pharmacia Biotech, Inc., Piscataway, N.J.). The biotinylated XPG-GST was seen as a 32 kDa discrete protein band.

To determine a suitable concentration of biotinylated XPG-GST protein which may be enough to saturate all streptavidin-binding sites on wells of a 96-well streptavidin-coated plate (Pierce, Rockford, Ill.), a validation of the streptavidin surface of streptavidin-coated plate was first carried out using biotinylated-HRP enzyme. Specifically, different dilutions of biotinylated enzyme HRP (biotin-HRP) (Sigma, Co., St. Louis, Mo.) stock solution were incubated for 1 hour at room temperature, washed 5 times with PBS (pH 7.4) containing 0.1% (v/v) Tween20). Then, 100 µl of substrate solution for HRP enzyme (Sigma Co., St. Louis, Mo.) was added, followed by 15 minutes of incubation at 25° C. To stop the reaction, 50 µl of stop solution (0.5 M $H_2SO_4$) was added. Absorbance was measured at 450 nm. Streptavidin-HRP (Sigma Co., St. Louis, Mo.) was used at different dilutions in 0.1% (v/v) polyoxyethylenesorbitoan Monolaurate in PBS (pH 7.4) (PBST) as a control to show non-specific protein-protein interactions. The results are shown in FIG. 5A.

Figure 5A:
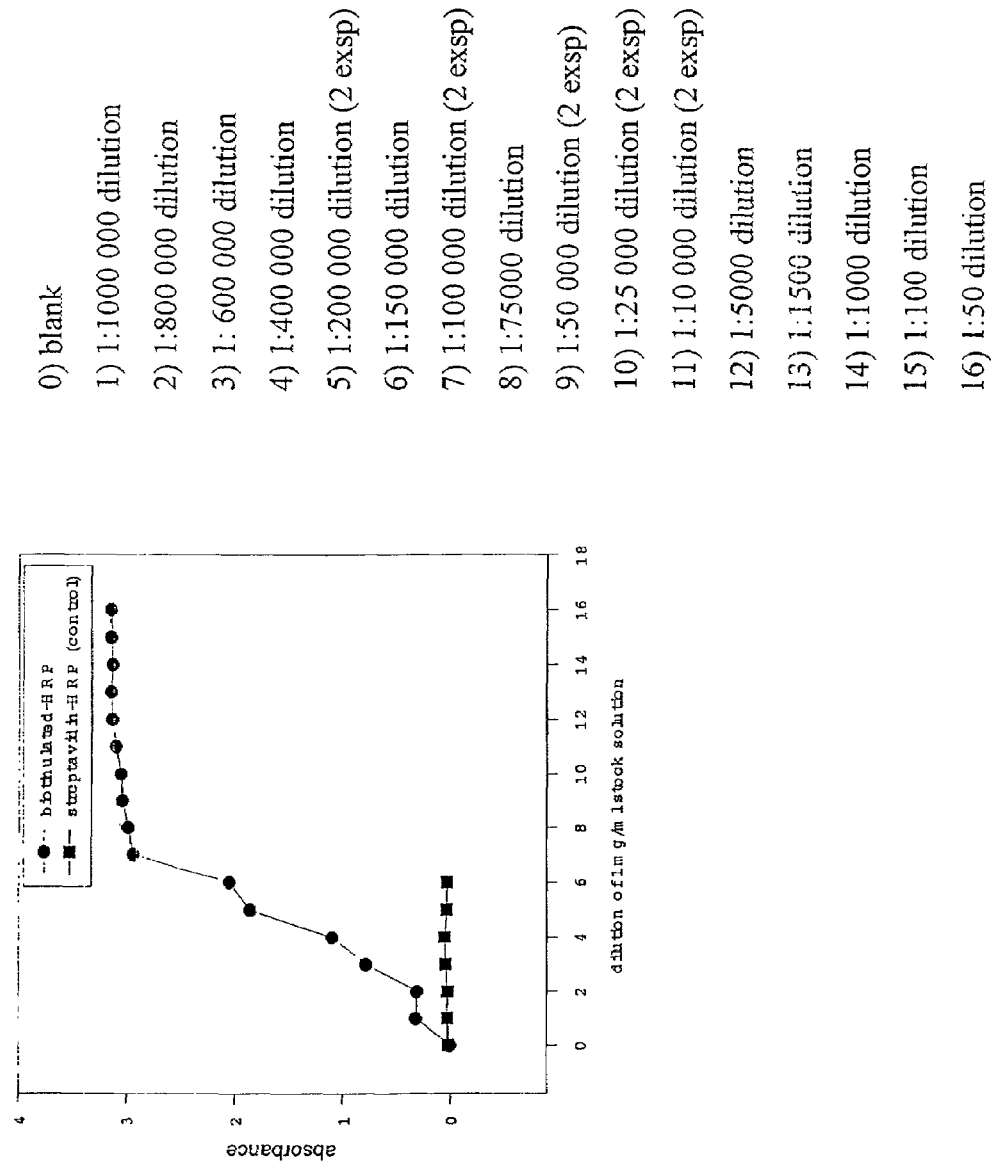
FIG. 5A shows the results of a validation study on the viability of the streptavidin surface of streptavidin-coated plates.

As shown in FIG. 5A, streptavidin-coated plates were found to be completely saturated by biotin-HRP even at 1:150,000 dilution per well.

Since the streptavidin-coated plate was completely saturated by biotin-HRP at 1:150,000 dilution, the same dilution of this enzyme was used for determination of a suitable concentration of biotinylated XPG-GST protein to use. Specifically, streptavidin-coated plate was first incubated for 1 hour with different concentrations of biotinylated XPG-GST protein (10-150 µg/ml) at 25° C. After washing 5 times with PBST, biotin-HRP was added in a 1:150,000 dilution. HRP-linked enzyme was detected by adding 3,3',5,5'-tetramethylbenzidin liquid substrate system for ELISA (Sigma) of substrate-reacting solution, and absorbance was measured at 450 nm. The results are shown in FIG. 5B.

Figure 5B:
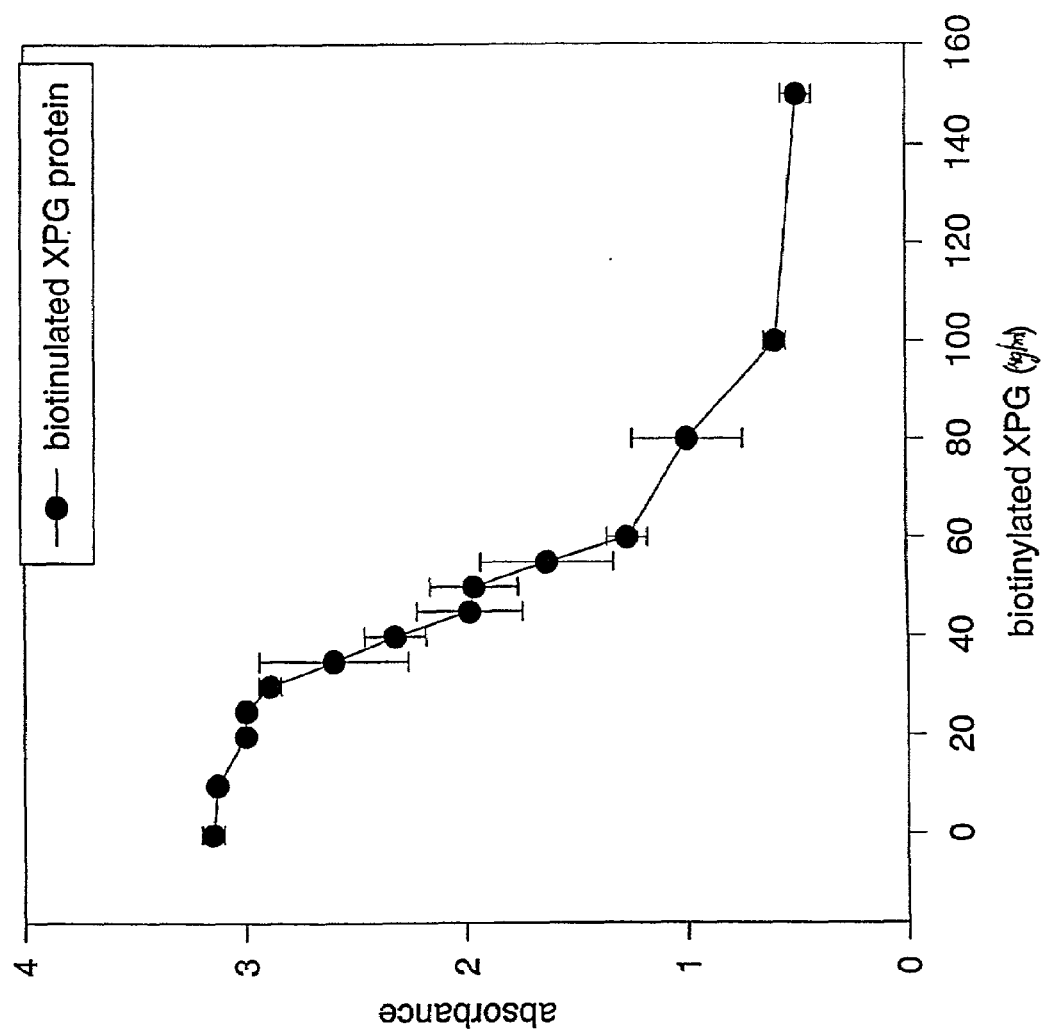
FIG. 5B shows the results of a study for determining the maximal binding capability of biotinylated XPG-GST protein to streptavidin-coated plates.

As shown in FIG. 5B, the optimal concentration of biotinylated XPG-GST protein that was required for saturation of all of the streptavidin-binding sites on the plate was 100 µg/ml.

B. ELISA

A streptavidin-coated plate was incubated with 100 µg/ml of biotinylated XPG-GST protein for 1 hour at 25° C. Then, the wells of the plate were washed with PBST and incubated with different dilutions of protein samples, isolated from MCF7 (ATCC No. HTB-22) (Michigan Cancer Foundation, Detroit, Mich.) and MCF10A (Michigan Cancer Foundation, Detroit, Mich.) breast cell lines. The protein samples were obtained as follows.

MCF7 and MCF10A were cultured according to the protocols provided by the American Type Culture Collection (ATCC). Briefly, MCF7 cell cultures were maintained in Dulbecco's Modified Essential Media (DMEM) supplemented with 5.0% (v/v) fetal bovine serum (FBS), 100 units/ml of penicillin, 100 µg/ml of streptomycin, and 1.0% (w/v) non-essential amino acids. MCF10A cultures were maintained in DMEM/F12 supplemented with 5.0% (v/v) $Ca^{++}$ horse serum, 10 mM HEPES, 10 µg/ml of insulin, 20 ng/ml of epidermal growth factor (EGF), 100 ng/ml of cholera enterotoxin, 0.5 µg/ml of hydrocortisone, 100 units/ml of penicillin, and 100 µg/ml of streptomycin. Both cell types were grown as monolayers at 37° C., in 5.0% $CO_2$ atmosphere. Semiconfluent (50-75%) cell cultures were harvested and washed three times with phosphate-buffered saline (PBS), and then pelleted using low-speed centrifugation, i.e., 200×g for 5 min at 4° C. The cell pellets were stored at −80° C. until use. Next, the DNA synthesome-enriched fraction, i.e., the P4 faction, was isolated from the pellets of the non-malignant (MCF10A) and malignant (MCF7) breast cell lines as described by Coll et al, *Oncol. Res.*, 8(10,11):435-447 (1996), and the protein concentration in the P4 fraction was determined by a colorimetric assay.

The protein profile of the P4 fraction isolated from MCF7 and MCF10A cells was analyzed by 12% (w/v) SDS-PAGE, Western blots using PCNA antibody, and densitometric analysis. More specifically, 5-300 µg of the samples were resolved in 12% (w/v) SDS-PAGE and transferred to nitrocellulose membrane. Western blot analysis was performed using a monoclonal PCNA antibody (Santa Cruz Biotechnology, Inc., Santa Cruz, Calif.). The values after scanning Western blot fluorograms, were expressed in Arbitary units (Au). Discrete protein bands were quantified using BIORAD GS 710 Imaging Densitometer. The results of the densitometric analyses are shown in FIG. 6, which reflects the average of three independent assays, expressed as means ±SE.

Figure 6:
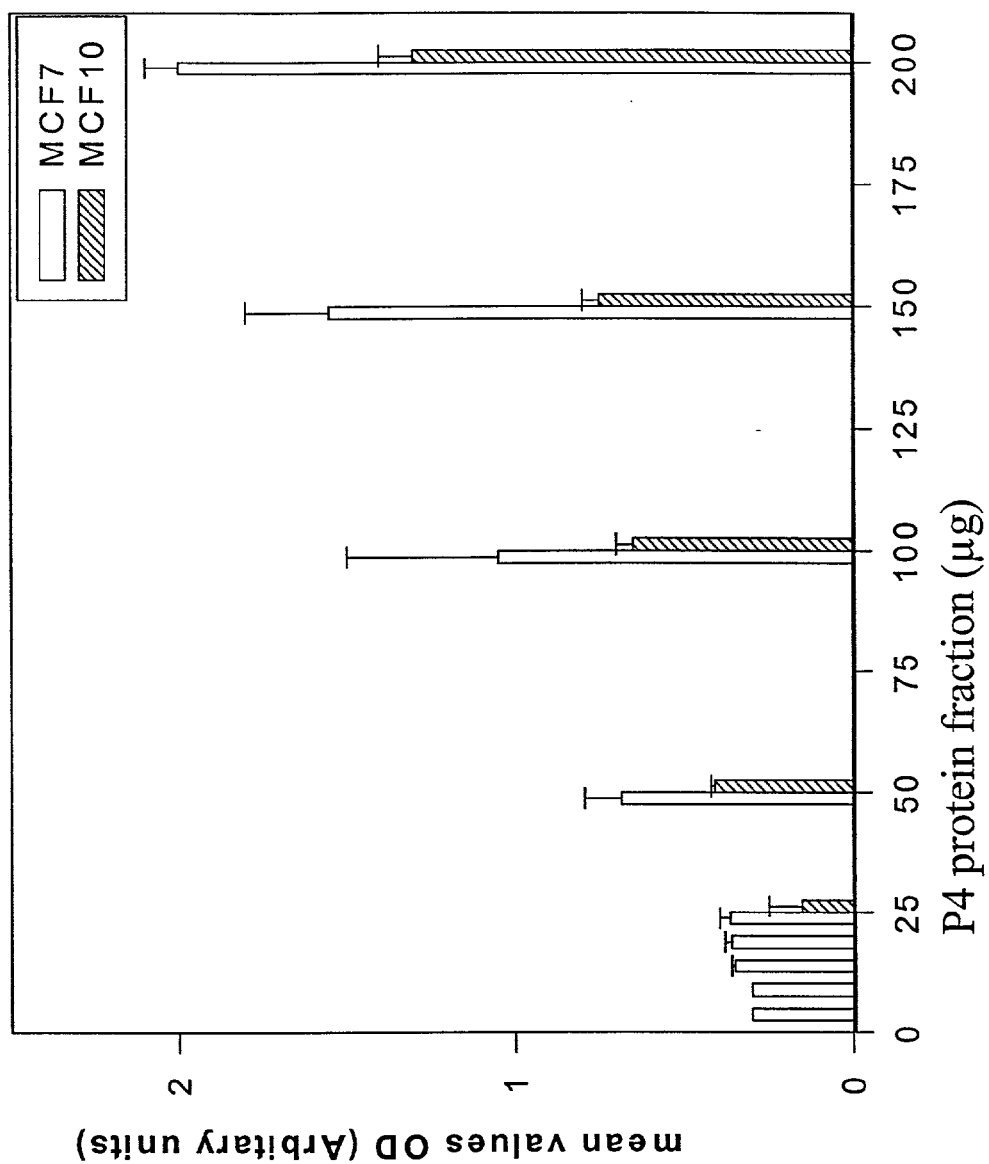
FIG. 6 shows densitometric analyses of total PCNA in P4 fractions from MCF7 and MCF10A cells.

As shown in FIG. 6, the results demonstrate that the P4 fraction isolated from MCF7 cells contains twice the PCNA protein than that found in the P4 fraction isolated from MCF10A cells. Even when this result was taken in consideration as discussed below, XPG peptide was still able to distinguish csPCNA in the two cell lines.

Thereafter, dilutions of the P4 fraction from MCF7 and MCF10A cells were added to the biotinylated XPG-GST coated plates. Incubation was performed overnight at 4° C. in buffer comprising 20 mM Tris-HCl (pH 7.4), 60 mM NaCl, 300 mM KCl, and 100 mM $KPO_4$ as described by Gary et al, supra. After washing with PBST, the wells were incubated with PCNA antibody labeled with HRP enzyme, for 1 hour at room temperature with constant agitation. The HRP-conjugated monoclonal PCNA antibody was obtained from Santa Cruz Biotechnology, Inc., Santa Cruz, Calif., and was used at dilution of 1:500 in 10% (v/v) blocking buffer comprising PBS (pH 7.4), 0.1% (w/v) BSA and 0.05% (v/v) Tween20. HRP enzyme was detected with TMB (3,3',5,5'-tetramethylbenzidin) (Sigma) substrate and absorbency was read at 450 nm. The results, which are shown in FIG. 7A, reflect the average of three independent assays, expressed as means ±SE.

Figure 7A:
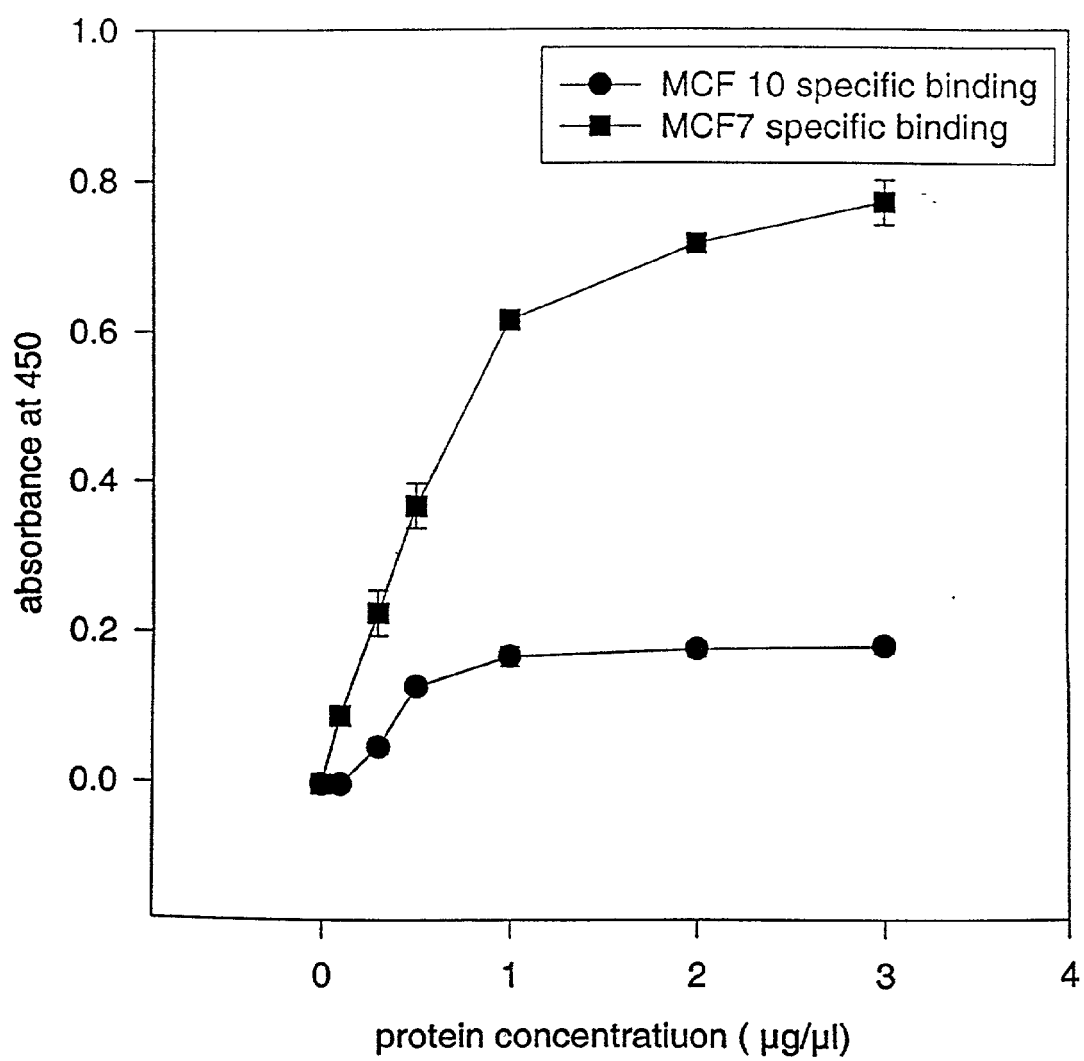
FIGS. 7A-7C show the results of ELISAs using MCF7 P4 and MCF10A P4 proteins.

As shown in FIG. 7A, XPG peptide is capable of distinguishing two forms of PCNA in the ELISA assay.

Next, serial dilutions of the P4 proteins were tested in duplicate in the ELISA and the mean value of absorbency was calculated and used for comparisons. Standard curves, representing the correlation between absorbency and the abundance of the malignant and non-malignant form of PCNA, were prepared and compared to each other. The results, which are shown in FIG. 7B (MCF7) and FIG. 7C (MCF10A), represented the mean values from three independent experiments.

Figure 7B:
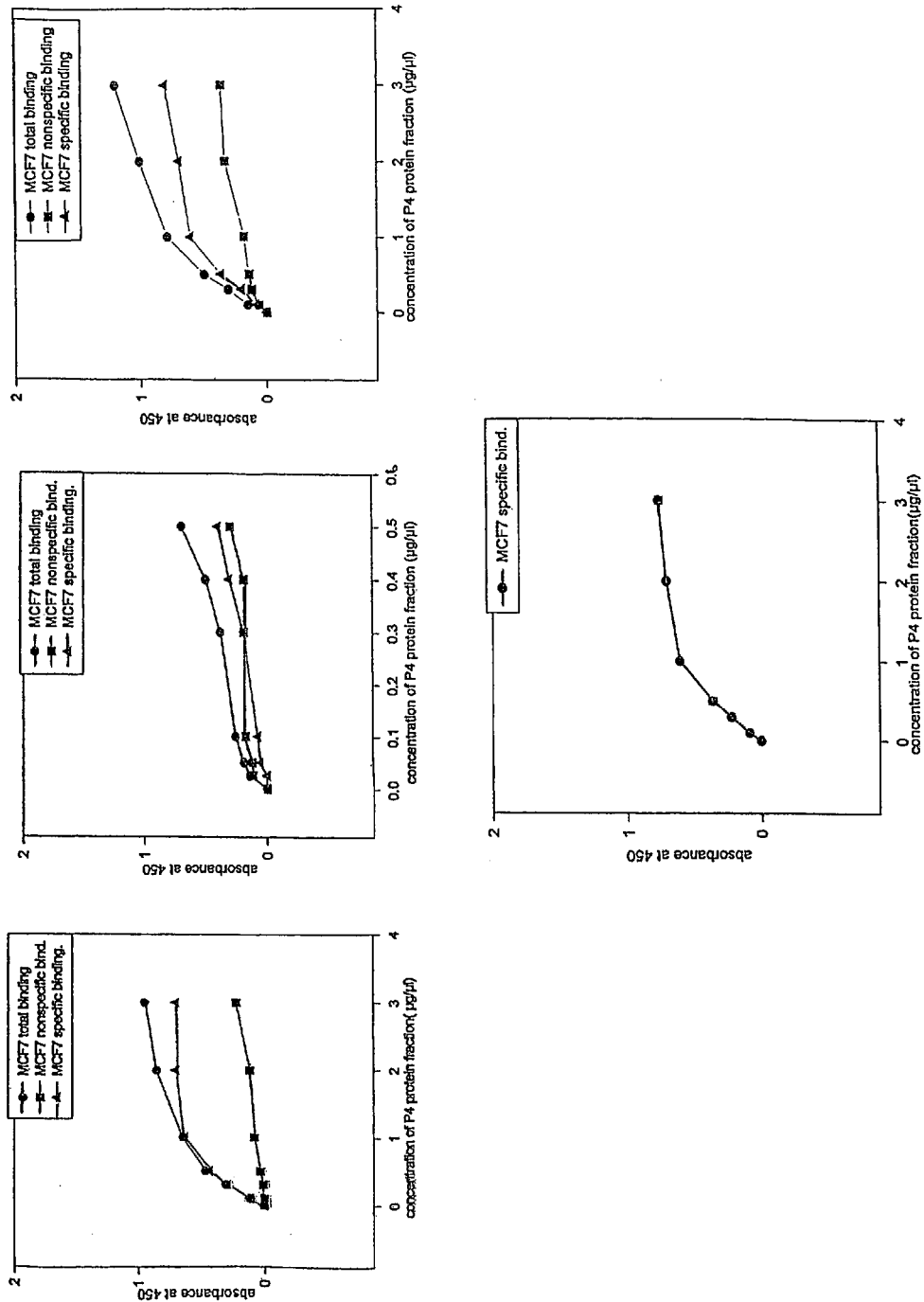
Figure 7C:
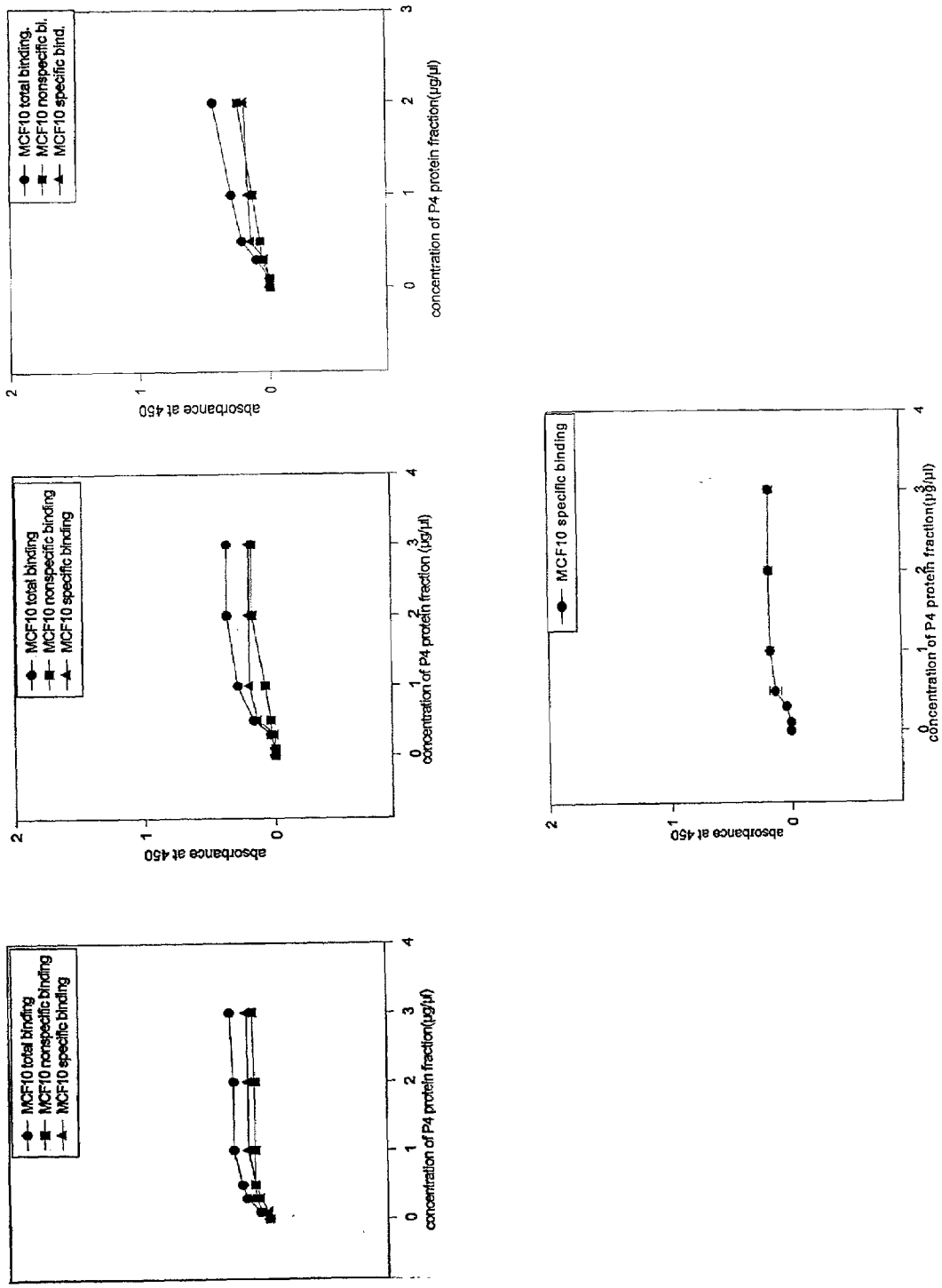

As shown in FIGS. 7B and 7C, the XPG peptide was found to have a higher binding affinity for csPCNA present in MCF7 breast cell lines.

Next, MCF10A and MCF7 cells were grown as described above. Semi-confluent (50-75%) cell cultures were harvested and washed three times with PBS, and then pelleted using low-speed centrifugation, i.e., 200×g for 5 min at 4° C. The cell pellets were stored at −80° C. until use. Next, the DNA synthesome-enriched fraction, i.e., the P4 faction, was isolated from the pellets of the non-malignant (MCF10A) and malignant (MCF7) breast cell lines as described by Coll et al, *Oncol. Res.*, 8(10,11):435-447 (1996).

The P4 fraction isolated from MCF7 and MCF10A cells was analyzed by ELISA. Specifically, the P4 fraction was added to biotinylated XPG-GST coated plates. Incubation was performed overnight at 4° C. in the buffer comprising 20 mM Tris-HCl (pH 7.4), 60 mM NaCl, 300 mM KCl, 100 mM $KPO_4$ as described above. After washing with PBST, the wells were incubated with PCNA antibody (Santa Cruz Biotechnology, Inc.), labeled with HRP enzyme, for 1 hour at room temperature with constant agitation. The PCNA antibody was used at dilution of 1:500 in 10% (v/v) blocking buffer comprising PBS (pH 7.4), 0.1% (w/v) BSA and 0.05% (v/v) Tween20. HRP enzyme was detected with TMB (3,3',5,5'-tetramethylbenzidin) (Sigma) substrate and absorbency was read at 450 nm. The amount of PCNA is indicated in arbitrary units. The results are shown in FIG. 8.

As shown in FIG. 8, and similar to the results in FIG. 6, the P4 fraction isolated from MCF7 cells contains twice the PCNA protein than that found in the P4 fraction isolated from the MCF10A cells. Even when this result was taken in consideration (where 10 µg of the P4 fraction isolated from MCF10 cells=1 arbitrary unit PCNA; and 5.0 µg of the P4 fraction isolated from MCF7 cells=1 arbitrary unit PCNA), XPG peptide was still able to distinguish csPCNA in the two cell lines.

While the invention has been described in detail and with reference to specific embodiments thereof, it will be apparent to one skilled in the art that various changes and modifications can be made therein without departing from the spirit and scope thereof.

What is claimed is:

1. A method for purifying cancer-specific Proliferating Cell Nuclear Antigen (csPCNA) comprising the steps of:
    (A) obtaining a tissue or body fluid sample comprising csPCNA;
    (B) contacting said sample with a peptide comprising the amino acid sequence LeuLysGlnLeuAspAla-GlnGlnThrGlnLeuArgIleAspSerPhePheArgLeu Ala-GlnGlnGluLysGluAspAlaLysArg (SEQ ID No: 1), wherein said peptide is immobilized on a solid support and binds to said csPCNA to form a peptide-csPCNA complex; and
    (C) isolating csPCNA from said peptide-csPCNA complex so as to purify said csPCNA.

2. The method of claim 1, wherein prior to step (B) the thus obtained tissue or body fluid sample of step (A) is subjected to a process comprising:
    (1) homogenizing cells constituting said tissue or body fluid to obtain a homogenate (H);
    (2) separating said H into a nuclear pellet fraction (NP) and a cytosolic fraction (S1);
    (3) extracting nuclei from said NP to obtain a nuclear extract (NE);
    (4) subjecting said S1 to centrifugation to obtain a post-mitochondrial cytosolic supernatant (S2);
    (5) subjecting said S2 to centrifigation to obtain a post-mitochondrial/post-microsomal cytosolic supernatant (S3);
    (6) combining said NE and said S3 to form an NE/S3 fraction, applying the resulting NE/S3 fraction to a weak anion exchange matrix column and collecting the flow through (PCFT);
    (7) applying the resulting PCFT to a hydrophobic chromatography matrix column, eluting the column with buffer comprising ethylene glycol and collecting the eluant (PSE);
    (8) dialyzing out ethylene glycol present in the PSE to obtain a dialyzate; and
    (9) applying the resulting dialyzate to a strong anion exchange matrix column, eluting with a dialyzate buffer comprising a salt gradient, and collecting and pooling PCNA-containing fractions to obtain said sample.

3. The method of claim 1 or 2, wherein said tissue or body fluid sample of step (A) further comprises native PCNA (nPCNA), said nPCNA does not bind to said peptide in step (B), whereas said csPCNA binds to said peptide in step (B) to form a peptide-csPCNA complex and in step (C) isolating

SEQUENCE LISTING

<160> NUMBER OF SEQ ID NOS: 1

<210> SEQ ID NO 1
<211> LENGTH: 28
<212> TYPE: PRT
<213> ORGANISM: Homo sapiens

<400> SEQUENCE: 1

Leu Lys Gln Leu Asp Ala Gln Gln Thr Gln Leu Arg Ile Asp Ser Phe
1               5                   10                  15

Phe Arg Leu Ala Gln Gln Glu Lys Glu Asp Lys Arg
                20                  25 csPCNA is effected using an elution buffer whereby csPCNA is eluted from said csPCNA-complex.

4. An immunoassay for detecting csPCNA comprising:
(1) contacting a test sample with a peptide comprising the amino acid sequence LeuLysGlnLeuAspAla-GlnGlnThrGlnLeuArgIleAspSerPheP heArgLeuAla-GlnGlnGluLysGluAspAlaLysArg (SEQ ID No: 1), which has been immobilized on a solid support so as to bind csPCNA to said peptide to form a peptide-csPCNA complex; and
(2) contacting said peptide-csPCNA complex with an anti-PCNA antibody and detecting binding of said antibody to said complex.

5. The immunoassay of claim 4, wherein said assay is an ELISA and said antibody is labeled with a detectable enzyme.

6. The imniunoassay of claim 5, wherein said enzyme is horse radish peroxidase.

7. The immunoassay of claim 5, wherein said peptide is a fusion protein comprising said peptide and Glutathione-S-Transferase.

8. The inimunoassay of claim 7, wherein said fusion protein is biotinylated and immobilized on said solid support via streptavidin-coated on said solid support.

9. The method of claim 1, wherein the tissue or body fluid sample obtained is afflicted with a cancer selected from the group consisting of carcinomas, sarcomas, lymphomas, and leukemias.

10. The method of claim 9, wherein the tissue or body fluid sample obtained is selected from the group consisting of cervical, mammary glands, esophageal, glial cells, lung, stomach, intestine, prostate, white blood cells, urine, serum, and whole blood.

11. The method of claim 1, wherein said peptide is a fusion protein comprising said peptide and at least one of Glutathione-S-Transferase, Calmodulin Binding protein, or oligo (6X) histidine.

12. The immunoassay of claim 4, wherein the test sample is afflicted with a cancer selected from the group consisting of carcinaomas, sarcomas, lymphomas, and leukemias.

13. The immunoassay of claim 12, wherein the test sample is obtained by selecting from the group consisting of cervical, mammary glands, esophageal, glial cells, lung, stomach, intestine, prostate, white blood cells, urine, serum, and whole blood.

14. The immunoassay of claim 4, wherein said immunoassay is selected from the group consisting of radioimmunoassay, dot blot assay, slot blot assay, immunoprecipitation, protein quantification, imunno-PCR, and Western blot.

15. The method of claim 1, further comprising the step of producing antibodies (monoclonal or polyclonal) specific for csPCNA from said isolated and purified csPCNA.

* * * * *